United States Patent
Lang

[11] Patent Number: 6,112,745
[45] Date of Patent: Sep. 5, 2000

[54] SOUND ABSORBER FOR A RESPIRATOR

[75] Inventor: Bernd C. Lang, Gauting, Germany

[73] Assignee: MAP Medizintechnik fur Arzt und Patient GmbH, Germany

[21] Appl. No.: 09/196,083

[22] Filed: Nov. 19, 1998

[30] Foreign Application Priority Data

Sep. 7, 1998 [DE] Germany ............... 193 40 760

[51] Int. Cl.[7] .................................................. A61M 16/00
[52] U.S. Cl. .................... 128/204.18; 128/207.14; 128/912
[58] Field of Search ............. 128/204.18, 202.27, 128/202.13, 202.16, 204.24, 912

[56] References Cited

U.S. PATENT DOCUMENTS

| | | | |
|---|---|---|---|
| 4,281,652 | 8/1981 | Miller | 128/204.25 |
| 4,463,755 | 8/1984 | Suzuki | 128/204.18 |
| 5,222,486 | 6/1993 | Vaughn | 128/200.24 |
| 5,284,134 | 2/1994 | Vaughn et al. | 128/200.24 |
| 5,315,991 | 5/1994 | Teves | 128/207.14 |
| 5,538,002 | 7/1996 | Boussignac et al. | 128/207.16 |
| 5,582,166 | 12/1996 | Lee | 128/207.14 |
| 5,937,851 | 8/1999 | Serowski et al. | 128/202.27 |
| 5,957,898 | 9/1999 | Jepson et al. | 604/256 |

*Primary Examiner*—John G. Weiss
*Assistant Examiner*—V. Srivastava
*Attorney, Agent, or Firm*—Ohlandt, Greeley, Ruggiero & Perle; George W. Rauchfuss, Jr.

[57] ABSTRACT

The present invention relates to a sound absorber for a respirator comprising a mask, breathing devices, a connecting tube and at least one carbon dioxide outlet. The sound absorber (16) essentially consists of an inner pipe (22) and an outer tube (24) extending at least partially over it. The inner tube (22) is provided with at least one essentially radially extending through channel (38) which runs into the annular channel (40) which extends axially between the inner pipe (22) and the outer pipe (24) and has a constant annular width. (FIG. 3).

11 Claims, 3 Drawing Sheets

SOUND ABSORBER FOR A RESPIRATOR

The present invention relates to a sound absorber for a respirator comprising a mask, breathing devices for providing breathing air, a tube for connecting the breathing devices with the mask and at least one carbon dioxide outlet.

Respirators according to the invention are devices which support or completely take over a patient's respiration. Conventional respirators essentially consist of a mask, which is placed over the mouth and/or nose of a patient, and a tube for connecting the mask with a breathing device (such as CPAP and BiPAP breathing devices) which serves for supplying breathing air. The connecting tube is flexible and may be mounted pivotally on both the mask and the breathing device.

Moreover, respirators are known which are provided with an intermediate element, which is provided with slots, between the mask and the tube in order to remove the carbon dioxide comprised in the breathing air at least partially from the respirator. The slots are for example arranged at a slant angle with respect to the direction of flow and have a width of approx. 0.2 mm. The provision of such slots is above all disadvantageous because of the relatively loud flow noises and since such respirators are hard to clean, the patient is under certain circumstances exposed to draughts flowing out of the slots and a specific discharge resistance can only be adjusted with extreme difficulties.

Furthermore, respirators are known which comprise a washing-out adapter with big slot- or hole-like flow cross-sections. The pressure is reduced from therapeutic pressure to ambient pressure within an intermediate element as shown in FIG. 1. The intermediate element essentially consists of an inner member 2 and an outer member 4. The pressure is reduced mainly within the flow channels 6 having low geometrical dimensions, i.e. length and geometrical distribution. The channels 8 adjacent to the flow channels 6 serve for air conduction but not pressure reduction. This type of respirator comprising the aforementioned intermediate element is most disadvantageous because the design of the flow channels 6 results in relatively loud flow noises and the intermediate element is hard to detach on account of its design.

It is therefore the object of the present invention to provide an improved sound absorber for respirators. This object is achieved by the features of the claims.

For solving this problem, the invention is based on the idea of providing the breathing tube of a respirator with a sound absorber in which the pressure is reduced over the longest possible path, i.e. essentially over the entire length and the entire circumference of an annular channel.

The respirator according to the present invention is therefore particularly advantageous vis-à-vis the prior art because of its silent operation, i.e. the low flow noises, and since it can easily be cleaned, the mask and the tube may quickly be connected, the tube is not subjected to stresses as it may be attached to a connecting piece of the mask pivotally around its longitudinal axis and the outgoing air is automatically led away from the patient so that the patient is not exposed to draughts. A further advantage consists in that the noise absorber according to the invention does not offer any problems in connection with the condensation of water.

The respirator according to the present invention will exemplarily be illustrated in the following by means of a preferred embodiment.

Figure 1:
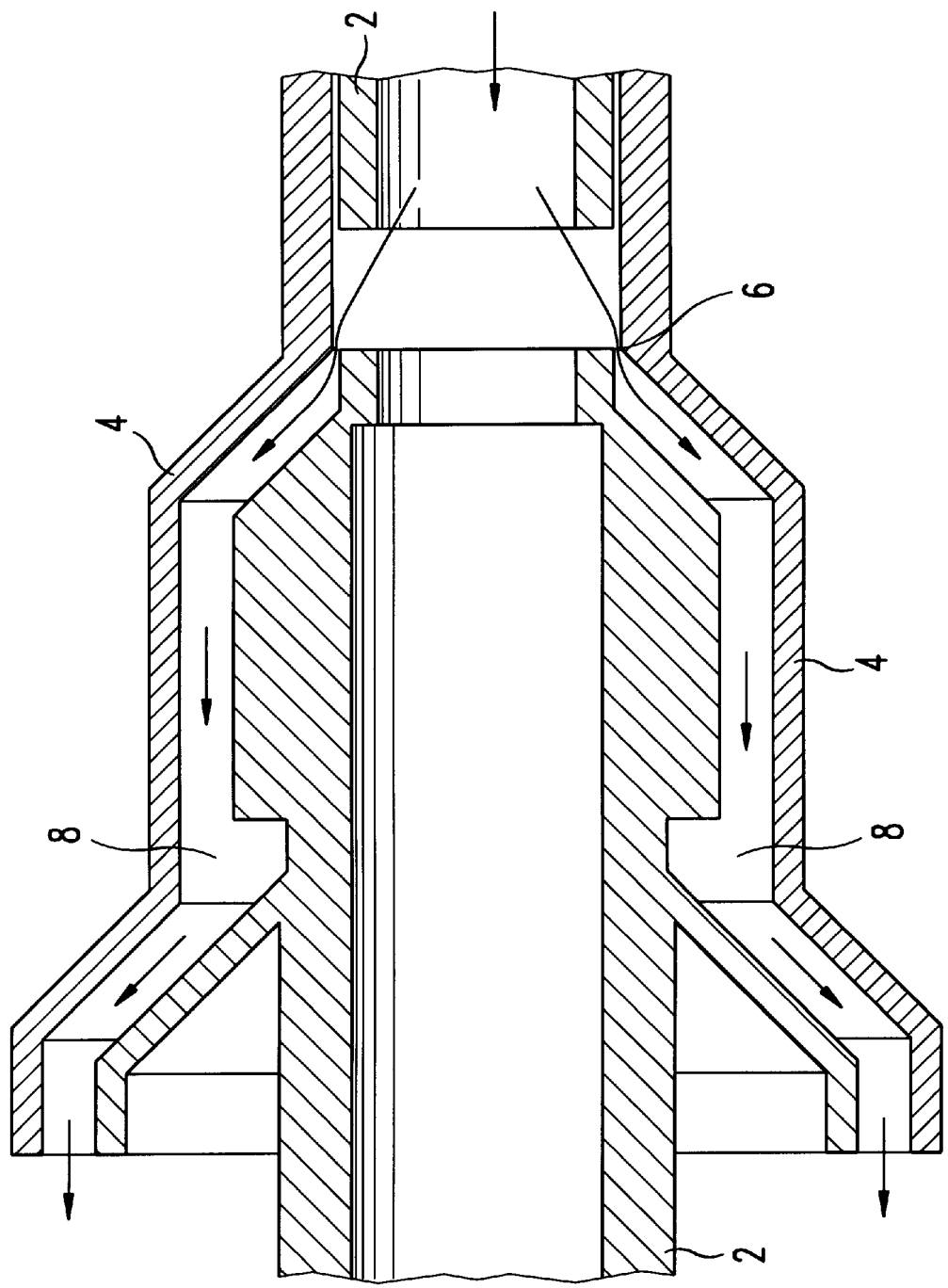
FIG. 1 shows the intermediate or noise-absorbing element of a prior art respirator provided in a breathing tube.
Figure 2:
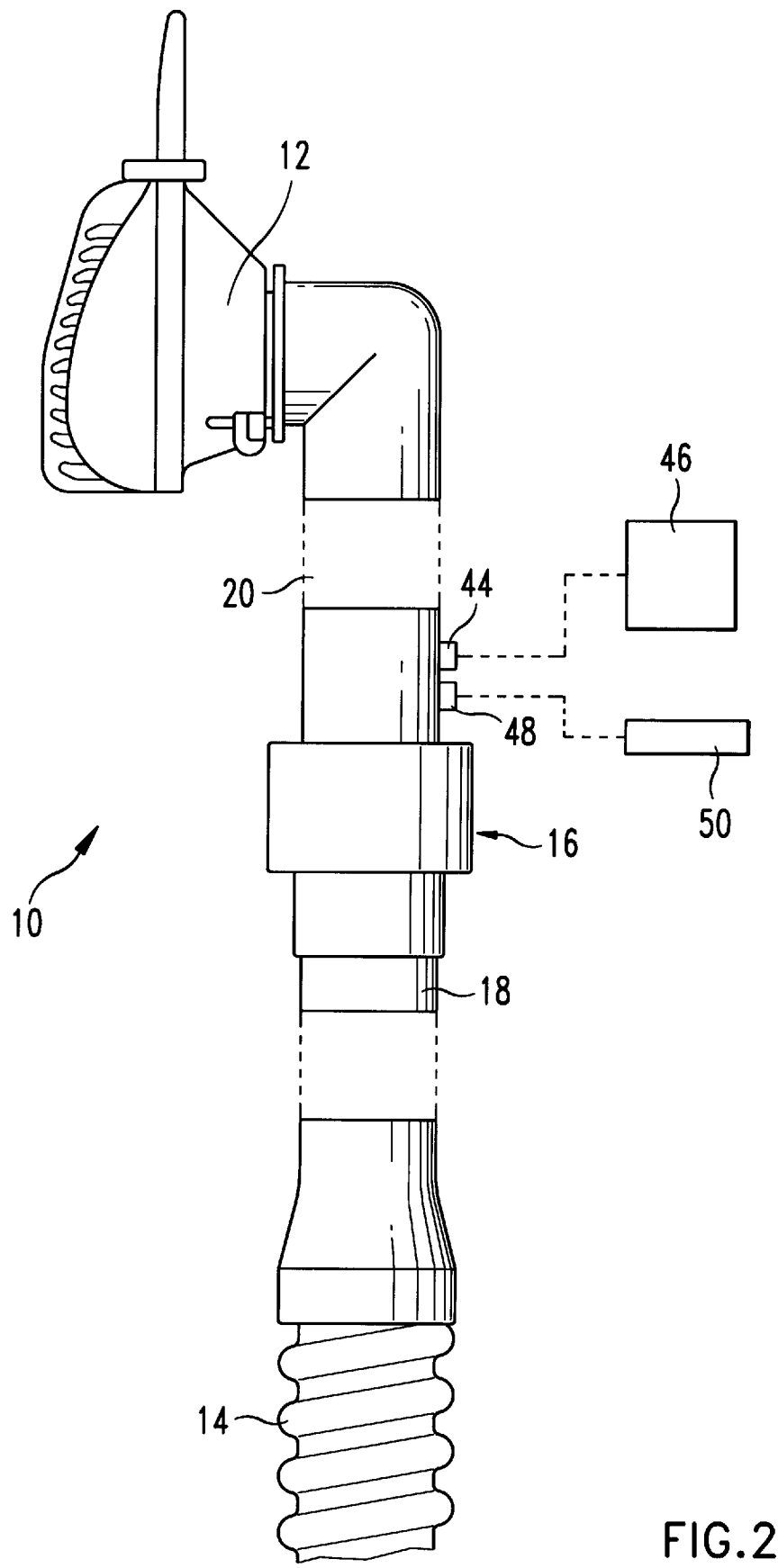
FIG. 2 shows the general plan of a respirator.

The respirator 10 shown in FIG. 2 essentially consists of a mask 12 which may be attached over a patient's mouth and/or nose, breathing devices (not shown) for providing the patient with breathing air, a tube 14 for connecting the breathing devices with the mask 12 and an intermediate element or noise absorber 16. The noise absorber 16 is provided between an end portion 18 of the tube 14 facing the mask 12 and a tube- or pipe-like end portion 20 of the mask 12 facing away from the mask 12. Preferably, the noise absorber 16 is provided in the vicinity of the mask 12.

Figure 3:
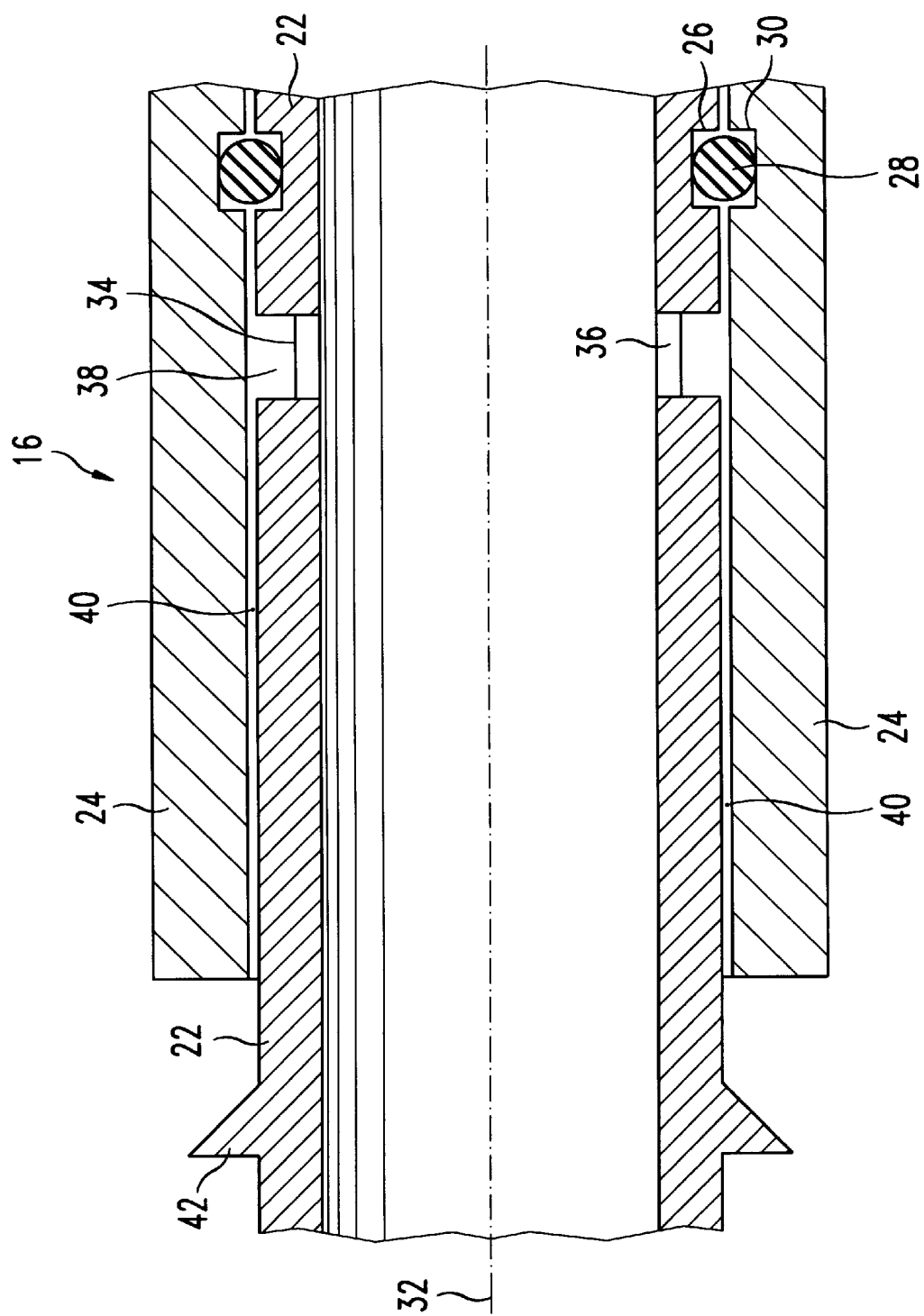
FIG. 3 shows a noise absorber according to the invention for a respirator.

The noise absorber 16, which is shown in more detail in FIG. 3, is designed such that it is suitable for "washing out", i.e. removing the carbon dioxide comprised in the breathing air and simultaneously absorbs noises effectively. The noise absorber 16 essentially consists of an inner pipe 22 at the end portion 18 of the tube 14 and an outer pipe 24 arranged thereover at the end portion 20 of the mask 12. The inner pipe 22 can be formed integrally with the end portion 18 or connected to it via suitable connecting means, preferably quick-release connecting means.

Preferably, the end of the inner pipe 22 facing the mask 12 is provided with a circumferential outer snap ring groove 26 into which a sealing or snap element 28, preferably a split washer or an O-ring is inserted. The outer pipe 24 has a corresponding circumferential inner snap ring groove 30 with which the sealing or snap element 28 engages. In addition to the sealing function, the sealing element 28 further serves for body sound decoupling between the mask-side and the tube-side elements of the respirator. Moreover, the sealing element 28 is an important component of a rapid connection means in that it axially fastens the inner pipe 22 to the outer pipe 24 by means of their respective snap ring grooves 26 and 30, but nevertheless permits relative rotations of the mask-side elements and the tube-side elements about a rotational axis 32. This embodiment permits a stress-free support of the breathing tube 14 when the patient moves, which is an important prerequisite for a good fit of the mask 12.

Moreover, in the vicinity of the upstream end of the inner tube 22, at least one radial aperture 34 is provided. However, preferably, a multitude of radial apertures 34 is provided around the circumference. Thus, the inner pipe 22 is held together at this location only by several connecting webs 36 in order to ensure the required stability of the sound absorber 16. Moreover, these webs 36 preferably have a reduced wall thickness, i.e. there is a difference between outer and inner diameter, so that a first annular space 38 is formed.

The carbon dioxide comprised in the expired air escapes through the radial apertures 34 into the annular space 38 and from there through a second annular space or channel 40 formed between the inner tube 22 and the outer tube 24 into the surroundings. The second annular channel 40 preferably has a constant annular width, i.e. there is a constant difference between outer and inner diameter. This second annular channel 40 preferably has a length of approx. 5 mm, a diameter of approx. 24 mm and a slot width of approx. 0.3 mm. Thus, the pressure of the removed breathing air is reduced along the entire length of the second annular channel 40, which leads to a considerable reduction in the noise emitted by the noise absorber 16 and the entire respirator.

Preferably, the downstream end of the inner tube 22 is provided with a circumferential guiding nose 42 which directs the outgoing expired air via the mounted tube away from the patient.

In a further embodiment of the respirator (schematically shown in FIG. 2), the inner pipe 22 and/or the outer tube 24 is/are provided with at least one connecting means 44 and 48 so that pressure measurements may be taken with the appropriate means 46 and/or further fluids, such as oxygen, may be provided e.g., by appropriate means 50.

Moreover, a further embodiment of the respirator (not shown) may be provided with fluid guide means which, depending on the flow direction in the intermediate element or the sound absorber 16, close the radial apertures 34 during inspiration and re-open them during expiration. Moreover, the fluid flow back into the tube can be at least impaired so that the majority of the carbon dioxide can escape through the radial apertures 34 via the first annular channel 38 or the second annular channel 40 in that during expiration the path back into the tube 14 is blocked by fluid guide means.

As already mentioned above, it is advantageous to permit relative motion of the tube 14 with respect to the mask 12. For this purpose, the inner tube 22 of the sound absorber 16 may form one end of the tube 14 or it may be attached to it. The outer pipe 24 may for example form the end portion 20 or be attached to it. Suitable locking or connecting means, preferably the aforementioned quick-release means permit rapid closing and opening of tie connection and rapid rotations of the elements relative to each other. However, the sound absorber can also be designed such that the inner pipe 22 is connected to both the tube-side end portion 18 and the mask-side end portion 20 and the outer pipe 24 is merely provided for forming the annular channel 40. For ensuring relative rotation of the tube 14 with respect to the mask 12, respective rapid connection means 26, 28 and 30 may in this case be arranged between the inner pipe 22 and at least one of the end portions 18 and 20.

What is claimed is:

1. Sound absorber (16) for a respirator (10) which is provided with an inner pipe (22) communicating with a breathing tube (14) and an outer pipe (24) at least partially extruding thereover at an end portion of a mask, wherein the inner pipe (22) is provided with at least one through channel (34) in the essentially radial direction, which channel runs into an annular channel (40) axially extending between the inner pipe (22) and the outer pipe (24) and having an essentially constant annular width.

2. Sound absorber (16) according to claim 1, wherein the inner pipe (22) is provided at a tube-side end portion (18) and the outer pipe at a mask-side end portion (20).

3. Sound absorber (16) according to claim 1, wherein the inner pipe (22) and the outer pipe (24) are designed as a connection between the mask (12) and the tube (14) which may be rapidly closed and re-opened.

4. Sound absorber (16) according to claim 1, wherein a sealing or snap element (28) is provided between the inner pipe (22) and the outer pipe (24).

5. Sound absorber (16) according to claim 4, wherein the sealing or snap element (28) engages with an outer snap ring groove (26) formed at the inner pipe (22) and an inner snap ring groove (30) formed at the outer pipe (24) in order to provide a connection which may rapidly be closed and re-opened.

6. Sound absorber (16) according to claim 1, wherein the wall thickness of the inner pipe (22) is reduced in the area of the through channel (34) so that a further annular channel (38) is formed which fluidally communicates with the annular channel (40) axially extending between the inner pipe (22) and the outer pipe (24).

7. Sound absorber (16) according to claim 1, wherein a plurality of through channels (34), which are separated from each other by webs (36), are provided around the circumference of the inner pipe (22).

8. Sound absorber according to claim 1, wherein a fluid guide nose (42) is provided at the downstream end of the inner pipe (22) outside the surrounding portion of the outer pipe (24).

9. Sound absorber (16) according to claim 8, wherein the flow guide nose (42) has an annular shape.

10. Sound absorber (16) according to claim 1 comprising at least one additional connection selected from at least one pressure measurement connection (44), at least one connection (48) for providing for introduction of fluids, or a combination of said connections.

11. Sound absorber (16) according to claim 10, wherein said additional connections are provided at the outer pipe (24).

* * * * *

UNITED STATES PATENT AND TRADEMARK OFFICE
CERTIFICATE OF CORRECTION

PATENT NO. : 6,112,745
DATED : September 5, 2000
INVENTOR(S) : Bernd C. Lanб

It is certified that error appears in the above-identified patent and that said Letters Patent is hereby corrected as shown below:

On the title page, at item [30], the priority application number which appears as "193 40 760.2" should read as --198 40 760.2--.

Signed and Sealed this

Seventeenth Day of April, 2001

Attest:

NICHOLAS P. GODICI

Attesting Officer     Acting Director of the United States Patent and Trademark Office